United States Patent [19]

Wade

[11] Patent Number: 4,939,310
[45] Date of Patent: Jul. 3, 1990

[54] CONVERSION OF METHANE TO HIGHER HYDROCARBONS

[75] Inventor: Steven R. Wade, Chertsey, England

[73] Assignee: The British Petroleum Company p.l.c., London, England

[21] Appl. No.: 255,786

[22] Filed: Oct. 11, 1988

[30] Foreign Application Priority Data

Oct. 17, 1987 [GB] United Kingdom ............... 8724373

[51] Int. Cl.$^5$ ........................... C07C 5/00; C07C 2/10
[52] U.S. Cl. ................................. 585/500; 585/654; 585/656; 585/700; 585/943; 585/750; 585/661
[58] Field of Search ............... 585/500, 654, 656, 700, 585/943, 661, 750

[56] References Cited

U.S. PATENT DOCUMENTS

| | | | |
|---|---|---|---|
| 4,443,649 | 4/1984 | Jones ................................. | 585/700 |
| 4,495,374 | 1/1985 | Jones et al. ....................... | 585/700 |
| 4,499,322 | 2/1985 | Jones et al. ....................... | 585/700 |
| 4,523,049 | 6/1985 | Jones et al. ....................... | 585/700 |
| 4,544,784 | 10/1985 | Sofranko et al. ................. | 585/700 |
| 4,547,607 | 10/1985 | Jones et al. ....................... | 585/700 |
| 4,547,610 | 10/1985 | Sofranko et al. ................. | 585/700 |
| 4,547,611 | 10/1985 | Jones et al. ....................... | 585/700 |
| 4,554,395 | 11/1985 | Jones et al. ....................... | 585/700 |
| 4,560,821 | 12/1985 | Jones et al. ....................... | 585/700 |
| 4,568,785 | 2/1986 | Jaecker et al. ................... | 585/700 |
| 4,665,260 | 5/1987 | Jones et al. ....................... | 585/700 |
| 4,695,668 | 9/1987 | Velenyi ............................. | 585/700 |
| 4,769,508 | 9/1988 | Gastinger et al. ................ | 585/500 |

FOREIGN PATENT DOCUMENTS

| | | |
|---|---|---|
| 0177327 | 4/1986 | European Pat. Off. . |
| 0253522 | 1/1988 | European Pat. Off. . |
| WO85/04866 | 11/1985 | World Int. Prop. O. . |

Primary Examiner—Patrick P. Garvin
Assistant Examiner—E. D. Irzinski
Attorney, Agent, or Firm—Brooks, Haidt, Haffner & Delahunty

[57] ABSTRACT

Methane is converted into higher hydrocarbons by contact at a temperature in the range from 500° to 1000° C. with a contact solid comprising a manganese oxide incorporating at least one of the elements tin, titanium, tungsten, tautalum, silicon, germanium, lead, phosphorus, arsenic, antimony, boron, gallium, indium, a lanthanide or an actinide. The contact solid is preferably promoted by either an alkali or alkaline earth metal, for example sodium.

10 Claims, No Drawings

CONVERSION OF METHANE TO HIGHER HYDROCARBONS

The present invention relates generally to a process for converting methane to higher hydrocarbons and in particular to the oxidative coupling of methane to higher hydrocarbons in the presence of manganese oxide-containing catalysts.

The use of manganese oxide as a catalyst for the oxidative coupling of methane to higher hydrocarbons is well known in the art. Thus, for example, U.S. Pat. No. 4,443,649 discloses a method for converting methane to higher hydrocarbon products ($C_2+$) which comprises contacting a gas comprising methane and a reducible oxide of manganese at a temperature within the range of about 400° to 1000° C., said contacting being carried out in the substantial absence of catalytically effective Ni, Rh, Pd, Ag, Os, Ir, Pt, Au and compounds thereof.

It is also known, for example from U.S. Pat. Nos. 4,544,787; 4,547,608 and 4,650,781 to use a manganese oxide-containing catalyst and a support material. U.S. Pat. No. 4,544,787 discloses the conversion of methane to higher hydrocarbons by contact with a contact agent produced by the method having the following steps: (a) combining hydroxylated magnesia and a component of silicon which forms silica and which is readily suspendible in a continuous medium, (b) contacting the combined components with a component of at least one metal, the oxide of which is reducible, and (c) calcining the contacted components to form the contact agent. U.S. Pat. No. 4,547,608 discloses contacting hydrocarbons, preferably a gas comprising methane, with a contact agent at conditions to convert the hydrocarbons, preferably at a temperature selected within the range of about 500° to about 1000° C., which agent comprises: (a) at least one reducible oxide of at least one metal, which oxide is reduced and produces higher hydrocarbon products and water when contacted with methane at the selected temperature, (b) a support comprising first and second oxides, preferably solid oxides, the first oxide comprising alkaline earth metal oxides, the second oxide selected from a group consisting of silica, alumina, and mixtures thereof, and the mole ratio of the first oxide to the second oxide being less than about 1:1, and (c) an alkali metal. U.S. Pat. No. 4,650,781 discloses a class of catalyst compositions comprising (a) Mn-containing oxides, (b) at least one alkali metal or compound thereof, and (c) at least one member of the group consisting of oxides of Zr, mixed oxides of Zr and Si, and mixed oxides of Zr and at least one alkaline earth metal.

U.S. Pat. No. 4,523,050 discloses the conversion of methane to higher hydrocarbons in the presence of oxygen by contacting a first hydrocarbon gas comprising methane and a second oxygen-containing gas with a contact solid which comprises at least one compound comprising Mn, Si and O, preferably at least one manganese silicate.

It is also known from, for example US. Pat. Nos. 4,449,322 and 4,523,049 to use alkali or alkaline earth metals as promoters for manganese oxide-containing catalysts.

Finally, it is known from U.S. Pat. No. 4,544,784 that at least one halogen component may be incorporated as a promoter into a contact solid comprising a reducible metal oxide, for example a manganese oxide. In an alternative embodiment at least periodically the reducible metal oxide and/or the reduced metal oxide is contacted with a halogen source.

The present invention provides a process for the conversion of methane into higher hydrocarbon by contact at a temperature in the range from 500° to 1000° C. with a contact solid comprising a manganese oxide characterised in that the contact solid additionally incorporates at least one of the elements tin, titanium, tungsten, tantalum, silicon, germanium, lead, phosphorus, arsenic, antimony, boron, gallium, indium, a lanthanide or an actinide.

The incorporation of the aforesaid elements can lead to a substantial increase in the yield of product $C_2+$ hydrocarbons.

The methane may be substantially pure methane or may be mixed with other gaseous paraffinic hydrocarbons, for example ethane, propane or butane. Inert diluents, for example argon, helium or nitrogen may also be employed if desired. Methane is preferably contacted continuously with the contact solid.

Preferably there is also fed a molecular oxygen-containing gas, which may be, for example, air or an air/oxygen mixture. Substantially pure oxygen may also be used as the oxygen-containing gas. The molecular oxygen-containing gas may be suitably be fed either continuously or intermittently. The oxygen-containing gas is preferably mixed with the methane feedstock prior to contact with the contact solid.

A suitable composition of the methane/oxygen-containing gas mixture at atmospheric pressure is a molar ratio of methane to oxygen of from 1.1 to 50 times the stoichiometric ratio of methane/oxygen for complete combustion to carbon dioxide and water. These limits are extendable if operation at pressures greater than atmospheric is envisaged or if the feed gases are preheated. It is preferred to operate at high methane to oxygen ratios within the aforesaid range because higher selectivities to $C_2$ hydrocarbons are obtained, though methane conversions are generally lower. Preferably, conditions are chosen which maximise the selectivity to $C_2+$ hydrocarbons and the methane conversion.

As an alternative to the molecular oxygen-containing gas, or in addition thereto, there may be fed a nitrogen-containing oxidant gas, for example dinitrogen monoxide ($N_2O$).

Suitably there may also be fed a source of halogen. Suitable sources of halogen include fluorine, chlorine, bromine or iodine and compounds thereof. Preferably the source of halogen is either chlorine or bromine or a compound thereof, for example hydrogen chloride. The source of halogen may suitably be fed either continuously or intermittently.

The contact solid comprises a manganese oxide, which is preferably trimanganese tetroxide ($Mn_3O_4$). The $Mn_3O_4$ may suitably be derived from manganese dioxide either during contact using a molecular oxygen-containing gas feed or in a separate reaction prior to contact with the feed, preferably the latter. Suitably formation of $Mn_3O_4$ from $MnO_2$ may be accomplished by calcining the $MnO_2$ at elevated temperature, for example 600° to 800° C., in the presence of a molecular oxygen-containing gas.

The contact solid preferably incorporates a promoter which may suitably be either an alkali or an alkaline earth metal. Suitably, the promoter metal may be either lithium, sodium, potassium, caesium, rubidium, calcium, mangesium, strontium or barium which may be incorporated in the form of the oxide or a compound thereof, for example a salt decomposable to the oxide. The preferred promoter metal is sodium. Preferably the promoter incorporates a halide-containing anion, for example chloride or bromide. A preferred promoter is sodium chloride, suitably in an amount in the range from 30 to 50 mol %.

The contact solid incorporates at least one of the elements tin, titanium, tungsten, tantalum, silicon, germanium, lead, phosphorus, arsenic, antimony, boron, gallium, indium, a lanthanide or an actinide. For the purpose of the present invention lanthanides are defined as those elements having an atomic number of from 57–71 and actinides are defined as those elements having an atomic number of from 89–103. Examples of suitable lanthanides and actinides include lanthanum, cerium and thorium. Preferred metals include tin, titanium, tungsten and tantalum. The metals may be incorporated in the contact solid by any suitable technique, for example by impregnation or coprecipitation of the elements, suitably in the form of salts, for example the nitrates, chlorides or alkoxides. Alternatively, the elementts may be admixed in oxide or other form with the other components of the contact solid. In the case of silicon, for example silica ($SiO_2$) or silicon carbide (SiC) may be mixed with the other components of the contact solid in the form of pellets, suitably of a similar size. Alternatively, in a preferred mixed form the other contact solid components are bound with finely divided silica, e.g. silica fines. A catalyst so-bound is advantageous because the resulting contact solid minimises sinter when exposed to the elevated temperatures at which methane conversion is operated. Titanium may suitably be incorporated in the form of titania ($TiO_2$).

The contact solid may be employed in the form of a fixed bed, a fluidised bed, a particulate bed or a recirculating bed, or in any other form.

The process is operated at a temperature in the range from 500° to 1000° C., preferably from 700 to 800° C. The pressures may suitably be in the range from 0 to 100 bar, preferably from 1 to 30 bar. The Gas Hourly Space Velocity (GHSV) as measured at STP may suitably be in the range from 100 to 100,000 $h^{-1}$, preferably from 600 to 5000 $h^{-1}$.

The process is preferably operated in a continuous manner. The process of the present invention will now be further illustrated by reference to the following Examples.

In the Examples there was used a 'high purity' form of manganese dioxide (GPR grade) containing 0.24 mol % Al and 0.8% K.

COMPARISON TEST 1

The manganese dioxide was calcined at 1000° C. for 6 hours giving a substantially phase pure form of $Mn_3O_4$ which was loaded with sodium chloride by an incipient wetness technique. A 50% loading of sodium chloride, i.e. a Na:Mn molar ratio of 1:2, was employed.

The contact solid so-obtained was tested for the conversion of methane to higher hydrocarbons under the conditions and with the results shown in the Table.

This is not an example in accordance with the present invention and is included only for comparison purposes.

COMPARISON TEST 2

2.3 mol % aluminium was loaded onto the catalyst of Comparison Test 1. The contact solid so-obtained was tested for the conversion of methane to higher hydrocarbons under the conditions and with the results shown in the Table. This is not an example in accordance with the invention and is included only for comparison purposes. The data presented in the Table demonstrate that aluminium is not effecitive in increasing the methane cconversion and ethylene selectivity.

EXAMPLES 1 to 5

Additional elements were loaded on to $Mn_3O_4$ (GPR grade) in a variety of forms, e.g. nitrate, chloride, alkoxide, and the resulting material was calcined at 1000° C. for 6 hours before loading with sodium chloride.

The contact solid so-obtained was tested for the conversion of methane to higher hydrocarbons under the conditions and with the results shown in the Table.

EXAMPLE 6

The contact solid obtained in Comparison Test 1 was mixed with pellets of silicon carbide of approximately equal size.

EXAMPLE 7

The contact solid obtained in Comparison Test 1 was bound with silica fines.

The contact solids obtained in Examples 6 and 7 were tested for the conversion of methane to higher hydrocarbons under the conditions and with the results shown in the Table.

TABLE

| EXAMPLE | CATALYST | BED TEMP (°C.) | CH$_4$ CONV. (%) | CARBON SELECTIVITIES (% C-mol) | | | |
|---|---|---|---|---|---|---|---|
| | | | | C$_2$H$_4$ | C$_2$H$_6$ | C$_3$+ | CO + CO$_2$ |
| Comp Test 1 | 50% NaCl/Mn$_3$O$_4$ | 799 | 37.5 | 24.0 | 12.1 | 4.2 | 57.7 |
| Comp Test 2 | 50% NaCl/Mn$_3$O$_4$ + 2.3 mol % Al | 775 | 29.3 | 8.5 | 7.5 | 0.9 | 83.1 |
| 1 | 50% NaCl/Mn$_3$O$_4$ + 2.3 mol % Sn | 791 | 38.4 | 30.6 | 9.4 | 6.4 | 53.7 |
| 2 | 50% NaCl/Mn$_3$O$_4$ + 2.3 mol % Ti | 814 | 41.8 | 31.3 | 10.4 | 7.1 | 51.2 |
| 3 | 50% NaCl/Mn$_3$O$_4$ + 2.3 mol % W | 816 | 40.7 | 31.2 | 12.3 | 7.2 | 49.2 |
| 4 | 50% NaCl/Mn$_3$O$_4$ + 2.3 mol % Ta | 804 | 44.1 | 34.6 | 9.8 | 9.4 | 46.1 |
| 5 | 50% NaCl/Mn$_3$O$_4$ + 5 mol % Si | 768 | 44.3 | 39.7 | 6.8 | 8.5 | 45.0 |
| 6 | 50% NaCl/Mn$_3$O$_4$/SiC | 780 | 46.2 | 35.8 | 8.6 | 9.7 | 45.9 |
| 7 | 50% NaCl/Mn$_3$O$_4$/SiO$_2$ (less than 50 micron) | 806 | 44.8 | 45.4 | 6.7 | 7.5 | 40.5 |

Feed CH$_4$/O$_2$ = 2.0, 100 ml/min, GHSV = 1200 h$^{-1}$
Catalyst 5 cm$^3$ 355–600 micron pellets.
⅛ inch outer diameter 316 stainless steel reactor
O$_2$ conversion greater than 99%

I claim:

1. A process for the conversion of methane into higher hydrocarbons which comprises contacting methane with a contact solid at a temperature in the range from 500° to 1000° C., said contact solid consisting essentially of:

(a) trimanganese tetroxide,
(b) an alkali or alkaline earth metal halide, and
(c) an element selected from the group consisting of tungsten, and tantalum.

2. A process according to claim 1, wherein there is also fed a molecular oxygen-containing gas.

3. A process according to claim 2 wherein the molecular oxygen-containing gas is mixed with the methane feedstock prior to contact with the contact solid.

4. A process according to claim 1, wherein the alkali or alkaline earth metal halide is sodium chloride.

5. A process according to claim 1, wherein the components of the contact solid are bound with finely divided silica.

6. A process according to claim 1, wherein the temperature is in the range from 700° to 800° C.

7. A process according to claim 1 wherein (c) is tungsten.

8. A process according to claim 1 wherein (c) is tantalum.

9. A process according to claim 4 wherein the sodium chloride is present in an amount in the range from 30 to 50 mol %.

10. A process according to claim 2 wherein the molar ratio of methane to oxygen-containing gas at atmospheric pressure is in the range from 1:1 to 50 times the stoichiometric ratio required for complete combustion.

* * * * *

UNITED STATES PATENT AND TRADEMARK OFFICE
CERTIFICATE OF CORRECTION

PATENT NO. : 4,939,310

DATED : July 3, 1990

INVENTOR(S) : STEVEN R. WADE

It is certified that error appears in the above-identified patent and that said Letters Patent is hereby corrected as shown below:

Col. 2, l. 26, after "may" and before "suitably" strike "be"

Col. 3, l. 23, correct the spelling of "elements"

Col. 3, l. 63, the words "The process of the present invention will now" should start a new paragraph Col. 4, l. 16, the words "The contact solid" should start a new paragraph Col. 4, l. 23, correct the spelling of "conversion"

Signed and Sealed this

Twenty-fifth Day of June, 1991

Attest:

HARRY F. MANBECK, JR.

Attesting Officer

Commissioner of Patents and Trademarks